(12) United States Patent
Rottensteiner et al.

(10) Patent No.: US 12,239,974 B2
(45) Date of Patent: Mar. 4, 2025

(54) MEASURING ARRANGEMENT FOR MEASURING THE TOTAL NITROGEN BOUND IN A MEASURING LIQUID

(71) Applicant: Endress+Hauser Conducta GmbH+Co. KG, Gerlingen (DE)

(72) Inventors: Ulrich Rottensteiner, Stuttgart (DE); Christian Cramer, Stuttgart (DE); Eva-Maria Petat, Stuttgart (DE); Thomas Baumgartner, Stuttgart (DE); Thomas Schipolowski, Stuttgart (DE); Ralf Bernhard, Stuttgart (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 612 days.

(21) Appl. No.: 16/997,137

(22) Filed: Aug. 19, 2020

(65) Prior Publication Data

US 2021/0053047 A1   Feb. 25, 2021

(30) Foreign Application Priority Data

Aug. 19, 2019   (DE) ..................... 10 2019 122 163.3

(51) Int. Cl.
*B01L 3/00*    (2006.01)
*G01N 21/33*   (2006.01)

(52) U.S. Cl.
CPC .............. *B01L 3/502* (2013.01); *G01N 21/33* (2013.01); *B01L 2200/10* (2013.01);
(Continued)

(58) Field of Classification Search
CPC ......... B01L 2200/10; B01L 2300/0627; B01L 2300/0858; B01L 2300/18;
(Continued)

(56) References Cited

U.S. PATENT DOCUMENTS 3,695,772 A * 10/1972 Spyropoulos .......... G01N 21/03
                                                        356/246
4,685,110 A *  8/1987 DeBell ..................... G02B 1/10
                                                        372/101
(Continued)

FOREIGN PATENT DOCUMENTS

CN         1104333 A    6/1995
CN         1629623 A    6/2005
(Continued)

OTHER PUBLICATIONS

Howell WO 2004/045772 english translation (Year: 2004).*
(Continued)

*Primary Examiner* — Jennifer Wecker
*Assistant Examiner* — Jonathan Bortoli
(74) *Attorney, Agent, or Firm* — Mark A. Logan; Endress+Hauser (USA) Holding, Inc.

(57) ABSTRACT

Disclosed is a measuring arrangement for measuring the total nitrogen bound (TN) in a measuring liquid, comprising: a radiation source emitting UV radiation; a radiation receiver configured to generate a signal that depends on the intensity of radiation impinging on the radiation receiver; a vessel having a first opening and a second opening opposite the first opening; a first window closing the first opening; and a second window closing the second opening. The first and second windows are transparent to the measuring radiation. The measuring radiation emitted by the radiation source propagates along a measuring path which extends from the radiation source through the first window, the vessel, and the second window to the radiation receiver. The measuring arrangement also includes a heating element in thermal contact with the vessel wall.

11 Claims, 4 Drawing Sheets

(52) U.S. Cl.
CPC .............. *B01L 2300/0627* (2013.01); *B01L 2300/0858* (2013.01); *B01L 2300/18* (2013.01); *B01L 2300/1883* (2013.01); *B01L 2300/1894* (2013.01)

(58) Field of Classification Search
CPC ..... B01L 2300/1883; B01L 2300/1894; B01L 3/502; G01N 21/0332; G01N 21/33; G01N 33/188
See application file for complete search history.

(56) References Cited

U.S. PATENT DOCUMENTS

| | | | | |
|---|---|---|---|---|
| 2007/0081159 | A1* | 4/2007 | Giffin | B01L 3/0275 356/440 |
| 2011/0110822 | A1* | 5/2011 | Adachi | G01N 35/025 422/82.09 |
| 2012/0099098 | A1* | 4/2012 | Webster | G01N 21/03 356/244 |
| 2012/0153149 | A1* | 6/2012 | Tixier | G01N 21/3563 250/559.01 |
| 2012/0192621 | A1* | 8/2012 | Ludwig | G01N 21/0332 73/25.01 |
| 2013/0265580 | A1* | 10/2013 | Vogl | G01N 21/05 356/440 |
| 2015/0168366 | A1* | 6/2015 | Volker | G01N 33/1806 422/549 |
| 2015/0198521 | A1 | 7/2015 | Moldt et al. | |
| 2016/0138908 | A1* | 5/2016 | Khan | B01L 3/5027 73/800 |

FOREIGN PATENT DOCUMENTS

| | | |
|---|---|---|
| CN | 102149810 A | 8/2011 |
| CN | 102401761 A | 4/2012 |
| CN | 103026210 A | 4/2013 |
| CN | 104034670 A | 9/2014 |
| CN | 104345034 A | 2/2015 |
| CN | 204142628 U | 2/2015 |
| CN | 104713768 A | 6/2015 |
| CN | 109645841 A | 4/2019 |
| DE | 202007002333 U1 | 5/2007 |
| DE | 102013108556 A1 | 2/2015 |
| DE | 102013114132 A1 | 6/2015 |
| DE | 202014105761 U1 | 2/2016 |
| DE | 102014115516 A1 | 4/2016 |
| EP | 3203169 A1 | 8/2017 |
| JP | 10288413 A | 10/1998 |
| WO | WO-2004054716 A1 * 7/2004 ............... B01L 7/52 |  |
| WO | 2015086147 A1 | 6/2015 |

OTHER PUBLICATIONS

Taslim "Rib fin effects on the overall equivalent heat transfer coefficient in a rib-roughened cooling channel" International Journal of Heat Exchangers, 1524-5608/vol. VI (Year: 2005).*

* cited by examiner

MEASURING ARRANGEMENT FOR MEASURING THE TOTAL NITROGEN BOUND IN A MEASURING LIQUID

CROSS-REFERENCE TO RELATED APPLICATION

The present application is related to and claims the priority benefit of German Patent Application No. 10 2019 122 163.3, filed on Aug. 19, 2019, the entire contents of which are incorporated herein by reference.

TECHNICAL FIELD

The present disclosure relates to a measuring arrangement for measuring the total nitrogen (TN) bound in a measuring liquid.

BACKGROUND

Wet-chemical analyzers are used, among other things, for determining ingredients of a measuring liquid in process measuring technology, in environment measuring technology and in the laboratory. These can be used to determine the concentration of individual substances, so-called analytes, in the liquid sample, e.g. ammonium, nitrate, phosphate. Such analyzers are often designed to add one or more reagents to the liquid sample in an automated manner, so that a chemical reaction with the analyte takes place in the liquid sample. The reagents are typically selected such that the chemical reaction is verifiable by physical methods, e.g., by optical measurements, using potentiometric or amperometric sensors, or by a conductivity measurement. The analyzer performs the corresponding measurement in the sample and ascertains the analyte concentration to be determined in the liquid sample based on the detected measurement signals. The chemical reaction may, for example, cause a coloring or a change of color which can be detected using optical means. In such cases, the intensity of the color is a measure of the measurand to be determined. The measurand may, for example, be ascertained photometrically by the analyzer by feeding electromagnetic radiation, such as visible light, from a radiation source into the liquid sample, and receiving it with a suitable receiver after transmission through the liquid sample. The receiver generates a measurement signal that depends on the intensity of the radiation received and which can be used to derive the measurand.

For monitoring the quality of water samples, so-called sum parameters are used, among other things, which are frequently detected as a measure of the nutrient content and/or the content of organically and inorganically bound carbon. Such parameters are, for example, the total carbon bound (TC), the total organic carbon (TOC), the chemical oxygen demand (COD), total nitrogen (TN or TNb) or total phosphorus (TP). Analyzers for determining these sum parameters frequently carry out a thermal or chemical disintegration of the liquid sample, with which the ingredients considered in the sum parameter are oxidized.

For example, an analyzer for determining the chemical oxygen demand of a liquid sample using a digestion reactor for chemically disintegrating a substance contained in a liquid sample is known from DE 10 2013 114 132 A1. The digestion reactor can be heated for digestion and is formed from a glass that is optically transparent to a photometric measurement following the digestion.

The total nitrogen (TN) is a sum parameter which is a measure of the proportion of nitrogen present in the sample, both in organic compounds, such as urea, peptides or proteins, and in inorganic compounds, such as ammonium, ammonia, nitrite or nitrate. Various methods exist for determining the total nitrogen bound in liquid samples. According to one of these methods, all nitrogen-containing compounds are oxidized to form nitrate, by means of a digestion using a strong oxidizing agent, for example peroxodisulfate, in alkaline solution at high temperatures, the solution is then cooled and neutralized, and optionally diluted, and the nitrate content of the solution is then photometrically determined. The wavelengths used for the photometric determination of the nitrate content are in the UVC range of the electromagnetic spectrum. This method is described, for example, in the Chinese Standard HJ 636-2012.

The digestion takes place at as high a temperature as possible in order to ensure that the bound nitrogen is completely converted into nitrate. Under excess pressure, temperatures of more than 100° C. can be reached. In order to ensure the optimal temperature control of the reaction, the digestion vessel should be made of an easily thermally conductive material and should be closable in a pressure-resistant manner.

Many materials commonly used in analyzers are not resistant to alkaline media at these temperatures. While the digestion reactor made of glass known from DE 10 2013 114 132 A1 is ideally suited for the digestion of a liquid sample with potassium dichromate in an acid solution described there in order to determine the chemical oxygen demand of the liquid sample, it is not possible to determine the total nitrogen according to the method described above using this reactor. While there are borosilicate or quartz glasses that are sufficiently resistant to hot alkaline solutions, they are not transparent to radiation in the UVC wavelength range. Other quartz glasses transparent to UVC radiation are not sufficiently resistant to hot alkaline solutions.

According to the current state of the art, analyzers for the total nitrogen determination therefore comprise different containers for the digestion and the photometric measurement. The digestion vessel is formed from a special, chemically resistant material, while the measuring cell is formed from a material optimized for photometric measurement. After the digestion has been carried out, and the subsequent cooling and neutralization, the liquid sample is transported from the digestion vessel into the measuring cell for the photometric measurement.

A disadvantage of such a solution is the larger number of components of the analyzer required as a result. This can lead to a more complex design and a higher maintenance effort compared to an analyzer comprising a single receptacle for digestion and measurement. The measurement duration is also prolonged by the transport of the liquid sample after digestion into another vessel for the measurement. In order to avoid entrainment effects, longer purge phases have to be factored in between the individual measurements when using separate vessels for the digestion and the photometric measurement, which additionally increases the overall measurement duration. Both the higher maintenance effort and the increase in the measuring duration ultimately lead to higher operating costs.

SUMMARY

The object of the present disclosure is therefore to provide a measuring arrangement for an automatic analysis device for determining the total nitrogen content of a liquid sample which avoids these disadvantages. In particular, an integration of an alkaline digestion and a subsequent photometric measurement in a single vessel is desirable.

The object is achieved according to the present disclosure by the measuring arrangement according to claim 1. Further advantageous embodiments are provided in the dependent claims.

The measuring arrangement according to the present disclosure for measuring the total nitrogen bound (TN) in a measuring liquid comprises:
- a radiation source, which is designed to emit at least measuring radiation of a wavelength or wavelength range in the UV wavelength range, in particular the UVC wavelength range;
- a radiation receiver, which is configured to generate a signal that depends on the intensity of measuring radiation impinging on the radiation receiver;
- a vessel comprising a vessel wall having at least one first opening and at least one second opening located opposite the first opening, a first window closing the first opening, in particular in a pressure-tight manner, and a second window closing the second opening, in particular in a pressure-tight manner, wherein the first and second windows are transparent to the measuring radiation;
wherein the radiation source and the radiation receiver are arranged with respect to the vessel such that at least a portion of the measuring radiation emitted by the radiation source propagates along a measuring path which extends from the radiation source through the first window, the vessel and the second window to the radiation receiver; and
- a heating element that is in thermal contact with the vessel wall.

Since the vessel comprises a vessel wall that has openings closed by windows, it can serve both as a reactor for a digestion of the nitrogen-containing components of the liquid sample in alkaline solution at high temperatures and as a measuring cell for the photometric determination of the concentration of nitrate formed by the digestion. More expensive materials, which are more difficult to process compared to conventional silicate glasses and which are transparent to UVC radiation, for example crystalline materials such as sapphire or magnesium fluoride, can be selected for the windows. Since the material for the vessel wall in the measuring arrangement according to the present disclosure does not have to be transparent to UVC radiation, a selection of suitable materials that are resistant to hot alkaline media and easily thermally conductive is obtained.

The measuring radiation in the UVC wavelength range may encompass one or more wavelengths between 200 nm and 300 nm. The measuring radiation for the determination of the total nitrogen bound preferably encompasses at least the wavelengths 220 nm and 275 nm.

In an advantageous embodiment, the vessel can comprise, on the outer side thereof, a plurality of cooling elements, for example cooling ribs, cooling vanes or cooling fins. For this purpose, the vessel wall can, on the outer side thereof, comprise a plurality of cooling elements or be in thermally conducting contact with a plurality of cooling elements. The cooling elements may be part of a heat sink that is in thermally conductive contact with the vessel wall.

This embodiment can advantageously be used for analysis methods such as the method for total nitrogen determination, with which a reaction mixture is produced from a liquid sample to be analyzed and an added reagent, the reaction mixture being heated to accelerate the chemical reaction and subsequently being cooled to a defined temperature for a measurement, for example an absorption measurement, by means of the radiation source and the radiation receiver.

The use of the cooling elements significantly reduces the time required to cool the reaction mixture.

The cooling elements and the vessel wall may be formed from the same material. In one possible embodiment, the cooling elements can be formed integrally with the vessel wall. In another embodiment, the cooling elements may be formed from a different material than the vessel wall. In this case, the vessel wall can be formed from a material that is optimized with respect to the chemical resistance thereof, while the cooling elements are formed from a material having optimized thermal conductivity and thermal capacity. The cooling elements can be connected to the vessel wall by means of fastening means, for example screws or rivets or a thermally conductive adhesive. In order to ensure good heat transfer between the vessel wall and the cooling elements, a heat-conducting layer, for example made of a heat conductive paste, can be arranged between the vessel wall and the cooling elements.

In a further embodiment, at least a section of the vessel is surrounded by thermal insulation.

The thermal insulation can be formed by a thermally insulating attachment, which surrounds a section of the vessel comprising cooling elements, in such a way that the cooling elements project into a space arranged between the vessel wall of the vessel and a wall of the attachment, wherein an opening is formed in the wall of the attachment, or between the wall of the attachment and the vessel, and leads into a lower region of the space surrounding the cooling elements.

The attachment may, for example, have the shape of a housing surrounding the vessel. The housing can be designed as a hood having one side open to the surrounding area. Such a hood may, for example, be placed on the vessel from above so that the open side thereof faces downwardly and surrounds at least a section of the vessel. The open side of the hood forms the aforementioned opening leading into the space surrounding the cooling elements.

In an advantageous embodiment, the vessel is arranged completely within the insulating attachment, in particular in such a way that the attachment protrudes markedly beyond the vessel toward the bottom. In all embodiments described here, the thermal insulation counteracts heat dissipation from the vessel during heating of the vessel and advantageously prevents, in particular hot air from escaping toward the top. The use of the terms "top" and "bottom" here and below refer to the orientation of the vessel and of the attachment intended during operation of the measuring arrangement.

As already mentioned, the cooling elements increase the efficiency of heat dissipation from the vessel during cooling, so that the reaction mixture present in the vessel can be cooled more quickly to a target temperature. On the other hand, the cooling elements increase the thermal mass of the overall device formed from the vessel and cooling elements and thus effect an extension of the heating time required for heating the reaction mixture to an elevated temperature. This can be counteracted by a suitable control of the heating power of the heating element. In addition, the thermally insulating attachment impedes heat transport by convection and thus contributes to the acceleration of the temperature increase of the vessel in heating phases.

In an advantageous refinement of this embodiment, the measuring arrangement can include a ventilation system comprising one or more fans, which is configured to generate a flow of air flowing around the cooling elements. For example, the one or more fans may be arranged at the opening leading into the space surrounding the cooling elements so as to transport air from the surrounding area into the space. This results in a flow of air flowing around the cooling elements in the attachment, by way of which heat is dissipated from the cooling elements. The ventilation system therefore makes it possible, even if the thermally insulating attachment is present during cooling phases, to effectively dissipate the heat from the cooling elements, and thereby accelerate the process of reaching a target temperature of the vessel during cooling phases.

In an advantageous embodiment, the wall of the attachment and the vessel wall of the vessel enclose an essentially U-shaped channel, which extends around the vessel and includes a first section extending upwardly parallel to a side wall of the vessel, a second section extending around an upper end of the vessel, and a third section extending downwardly parallel to a side wall of the vessel, wherein the opening forms an inlet opening at one end of the channel, and wherein the channel has an outlet opening at the other end thereof. In this embodiment, the ventilation system is arranged at the inlet opening. During operation of the ventilation system, in this embodiment a gas flow forms from the inlet opening through the channel in the direction of the outlet opening, which flows around the cooling elements and thus dissipates heat from the cooling elements.

The inlet opening and the outlet opening are advantageously arranged in the lower region of the attachment, ideally at the lowest point of the attachment. Advantageously, the outlet opening and the inlet opening are arranged essentially at the same height in order to avoid stack effects.

The measuring device can comprise an electronic control unit, in particular for carrying out analyses in an automated manner. The ventilation system and the heating element may be connected to the control unit. The control unit may be configured to control the heating element and the ventilation system in accordance with a predefined operating program. Advantageously, the control unit is designed to switch off the ventilation system during heating phases, in which the heating element is operated for heating the vessel, and to switch on the ventilation system during cooling phases, in which the heating element is shut off. In this way, both heating times and cooling times of the vessel can be optimally reduced.

The vessel can include at least one liquid inlet, which can be fluidically connected to a sample receiver containing the measuring liquid. A liquid sample, i.e. a predefined volume of the measurement liquid to be analyzed, can be introduced into the vessel via the liquid inlet. In addition to the liquid inlet, the vessel may include at least one pressure equalization opening. This enables pressure equalization when liquid is introduced into the vessel or when liquid is discharged from the vessel via the at least one liquid inlet.

The measuring arrangement can furthermore include a liquid container containing a digestion reagent having a pH of at least 12, wherein the liquid container can be fluidically connected to the liquid inlet. The liquid container can be connected to the liquid inlet of the vessel via a fluid line. A valve can be arranged in the fluid line, which selectively blocks or allows a transport of digestion reagent from the liquid container into the vessel. The digestion reagent can be a solution comprising one or more substances that chemically react with the nitrogen-containing compounds in the liquid sample. In the case of the above-described method according to the standard HJ 636-2012, the digestion reagent contains a strong oxidizing agent, such as peroxodisulfate, which oxidizes nitrogen-containing compounds present in the liquid sample in alkaline solution to form nitrate. The measuring arrangement may comprise further liquid containers, which can be fluidically connected to the liquid inlet of the vessel. These can contain further reagents required for the digestion or the detection of the nitrate formed by the digestion, standard solutions for calibration measurements, diluents or cleaning liquids.

The vessel wall can comprise a metal, a metal alloy, a ceramic or a high-performance plastic. Advantageously, the metal, the metal alloy, the ceramic or the high-performance plastic is not chemically attacked by the digestion reagent, which can have a pH value between 12 and 14, at a temperature of up to 130° C., in particular between 0 and 130° C. Machining processes, which ensure high accuracy and reproducibility, can be used for the processing of metals or metal alloys. High-performance plastics are, for example, thermoplastics, which have improved chemical resistance and temperature resistance compared to standard engineering plastics. It is also possible for the vessel wall to be made of a combination of the aforementioned materials, for example of a metal-coated ceramic or a plastic-coated or ceramic-coated metal, or a metal or a metal alloy comprising one or more metal and/or ceramic and/or plastic coatings.

If the vessel wall comprises a metal or a metal alloy, it may comprise, for example, titanium, gold, stainless steel (for example V4A steel) or Hastelloy. As mentioned, the vessel wall can be formed from several materials, for example by comprising a base material and a coating applied to the base material or several coatings applied to the base material. The vessel wall can also be processed by way of a surface treatment, for example by mechanically generated polishing, electropolishing or anodization.

In an advantageous embodiment, the first and the second windows can include, at least in a region of the windows facing the interior of the vessel, a material that is transparent to the measuring radiation, in particular in the UVC wavelength range, and that is chemically stable with respect to hot liquids up to 130° C. that have an alkaline pH value, in particular a pH value between 12 and 14. This material may be one of the materials sapphire, diamond, magnesium fluoride, calcium fluoride or barium fluoride. The windows can consist entirely of one of these materials. Alternatively, the windows can comprise a base body, which is made of a material that is transparent to UVC radiation, but is not stable with respect to hot alkaline media up to 130° C., and which, at least on the surface thereof facing the interior of the vessel, includes a coating made of a material that is stable against such media and, at the same time, is transparent to UVC radiation. This coating can, for example, be made of the aforementioned materials of sapphire, diamond, magnesium fluoride, calcium fluoride or barium fluoride. In this case, the base body can be formed from quartz glass.

The first and the second windows can each have two plane-parallel surfaces extending essentially perpendicularly to the radiation path.

Alternatively, the first and/or the second windows can each have at least one curved surface, in particular an optically effective surface for the beam shaping of the measuring radiation. The curved surface may be formed as a convex or concave, spherical or aspherical surface.

The measuring arrangement can furthermore comprise:
a first liquid path extending from the sample receiver to the at least one liquid inlet;
a second liquid path extending from the liquid container to the at least one liquid inlet;

at least one metering unit, which comprises at least one pump and/or at least one valve arranged in the first and/or second liquid paths and is configured to transport a predefined amount of liquid along the first liquid path into the vessel, and is furthermore configured to transport a predefined amount of liquid from the liquid container along the second liquid path into the vessel; and an electronic control unit, which is configured to control the metering unit to transport measuring liquid and digestion reagent into the vessel, to control the heating element for controlling a temperature of liquid present in the vessel, and to excite the radiation source to emit the measuring radiation and detect and process signals of the radiation receiver.

Advantageously, the measuring arrangement can form an automatic analyzer or be an integral part of an automatic analyzer. The analyzer can comprise a housing designed as a cabinet, in which the vessel serving as a digestion reactor and measuring cell is arranged. In addition to the digestion reactor, other parts of the measuring arrangement, for example liquid vessels, fluid lines, pumps, valves and the electronic control unit, can also be arranged in the housing. An input unit, which can, for example, comprise keys and a display or a touch screen, can be used to operate the electronic control unit.

The electronic control unit can comprise an evaluation program, which it can execute to determine values of the total nitrogen bound of the measuring liquid from the signals of the radiation receiver.

BRIEF DESCRIPTION OF THE DRAWINGS

The present disclosure is explained in further detail below on the basis of the exemplary embodiments shown in the figures. The following are shown.

DETAILED DESCRIPTION

Figure 1:
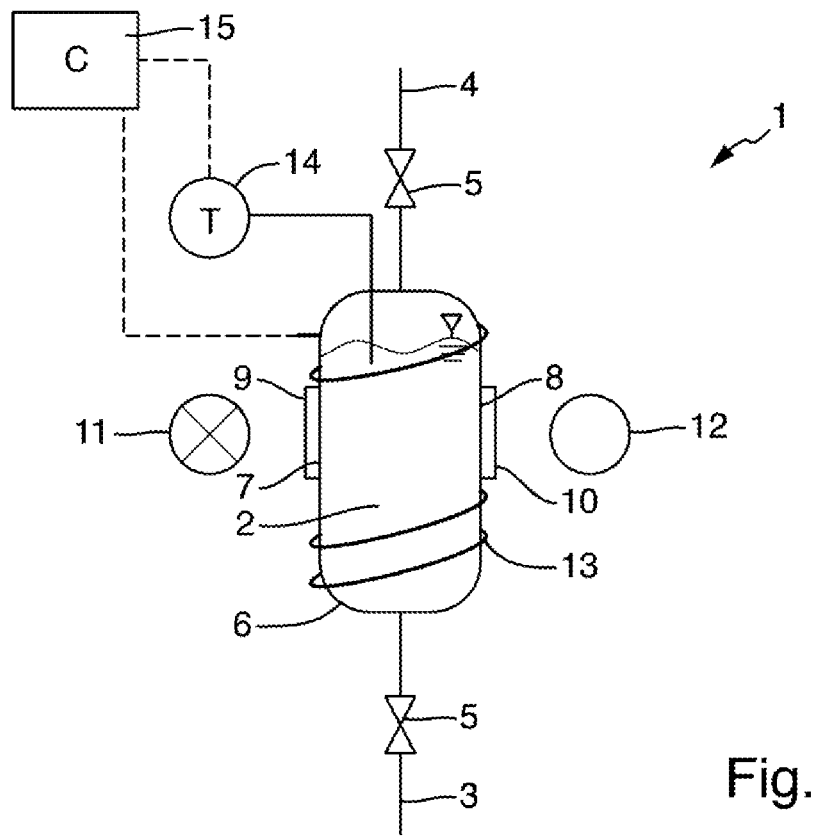
FIG. 1 shows a schematic longitudinal sectional view of a measuring arrangement according to a first embodiment.

FIG. 1 schematically shows, in a longitudinal sectional view, a measuring arrangement 1 for determining the total nitrogen content of a liquid sample. The measuring arrangement 1 comprises a vessel 2, which in the present example is essentially cylindrical and into which a fluid line 3 and a pressure equalization line 4 lead. The fluid line 3 and the pressure equalization line 4 each comprise a valve 5 by means of which they can be selectively blocked or released.

If both lines are blocked by the valves 5, the vessel 2 is closed with respect to the surrounding atmosphere in a pressure-tight manner.

The vessel 2 comprises a housing wall 6, which encloses an interior and, in the present example, is formed from a metal or a metal alloy, for example of titanium, gold or stainless steel. The housing wall 6 has a first opening 7 and a second opening 8 located opposite the first opening 7. A first window 9 is inserted into the first opening 7, and a second window 10 is inserted into the second opening 8. The windows 9 and 10 are made of a material that is transparent to radiation in the UVC wavelength range, in particular to radiation of the wavelengths between 220 nm and 280 nm. In the present example, the windows 9 and 10 are made of sapphire. The windows 9 and 10 are sealed in a pressure-tight manner with respect to the housing wall 6, for example by means of O-ring seals, so that even in the event that the liquid level, as shown in FIG. 1, is above the windows 9, 10, or an overpressure is present in the interior of the vessel 2, no liquid escapes from the vessel 2 to the outside. In the present example, the windows 9, 10 each have two mutually opposing plane-parallel surfaces. In an alternative embodiment, they can also have curved surfaces, for example they can be designed as lenses.

The measuring arrangement 1 furthermore comprises a radiation source 11 and a radiation receiver 12 which are arranged opposite one another in relation to the openings 7 and 8 in the housing wall 6 of the vessel 2 in such a way that measuring radiation emitted by the radiation source 11 propagates along a measuring path extending between the radiation source 11 and the radiation receiver 12. The measuring path extends through the first window 9, the vessel inner and the second window 10 in the process. Measuring radiation propagating along the measuring path thus interacts with the liquid present in the vessel 2 and is absorbed by the analyte, which may be present in the liquid. In the present example, a UV flash lamp serves as the radiation source 11. One or more Si photodiodes for detecting UV radiation are used as the radiation receiver 12. In the present example, the radiation receiver 12 is configured to detect radiation of individual wavelengths, for example 220 nm and 275 nm. For this purpose, a filter and/or beam splitter device can be provided in a manner known to the person skilled in the art, which makes it possible to detect the radiation of selected wavelengths, or selected wavelength ranges, using individual photodiodes or other suitable detection elements.

For setting a temperature in the vessel 2, the measuring arrangement 1 comprises a heating element 13, which in the present example comprises a heating wire that is electrically insulated with respect to the metallic housing wall 6. The heating wire extends helically around the housing wall 6. In the present example, a temperature control system is provided, which comprises a temperature sensor 14 detecting the temperature in the interior of the vessel 2 and a controller 15 that is configured, based on the signals of the temperature sensor 14, to set a heating power of the heating element 13 in such a way that a predefined target temperature of the interior of the vessel or of the liquid present in the vessel 2 is reached. The introduced heating power can additionally be controlled in such a way that the target temperature is reached at a predefined point in time.

Figure 2:
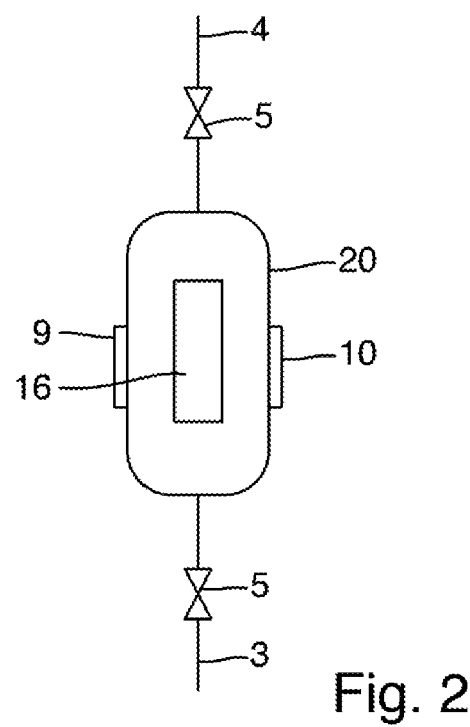
FIG. 2 shows a schematic longitudinal sectional view of a measuring arrangement according to a second exemplary embodiment.

FIG. 2 schematically shows an alternative embodiment of the vessel 20 and the heating element 13. Components designed identically to the corresponding components of the measuring arrangement 1 shown in FIG. 1 are denoted by the same reference numerals as in FIG. 1. The vessel 20 comprises a housing wall 6 in which windows 9 and 10 are arranged in openings. The windows 9, 10 are made of a material that is transparent to UVC radiation, for example $MgF_2$. A fluid line 3, which can be blocked by means of a valve 5, and a pressure equalization line 4, which can also be blocked by means of a valve 5, lead into the vessel 20. In the present example, the housing wall 6 is made of a metal alloy, for example Hastelloy. In contrast to the exemplary embodiment illustrated in FIG. 1, a heating resistor 16 attached to the outer side of the housing wall 6 serves as the heating element for controlling the temperature of a liquid present in the interior of the vessel 20 in the present exemplary embodiment. This heating resistor can be connected to a temperature regulator (not shown in FIG. 2). The temperature regulator can furthermore be connected to a temperature sensor, which is likewise not shown in FIG. 2 and which detects measured temperature values representative of the temperature of the liquid present in the vessel 20 and outputs it to the temperature regulator. The temperature regulator can be designed to adjust a heating power of the heating resistor 16 based on the measured temperature values in such a way that a desired target temperature of the liquid is reached and maintained for a predefinable period of time.

Figure 3:
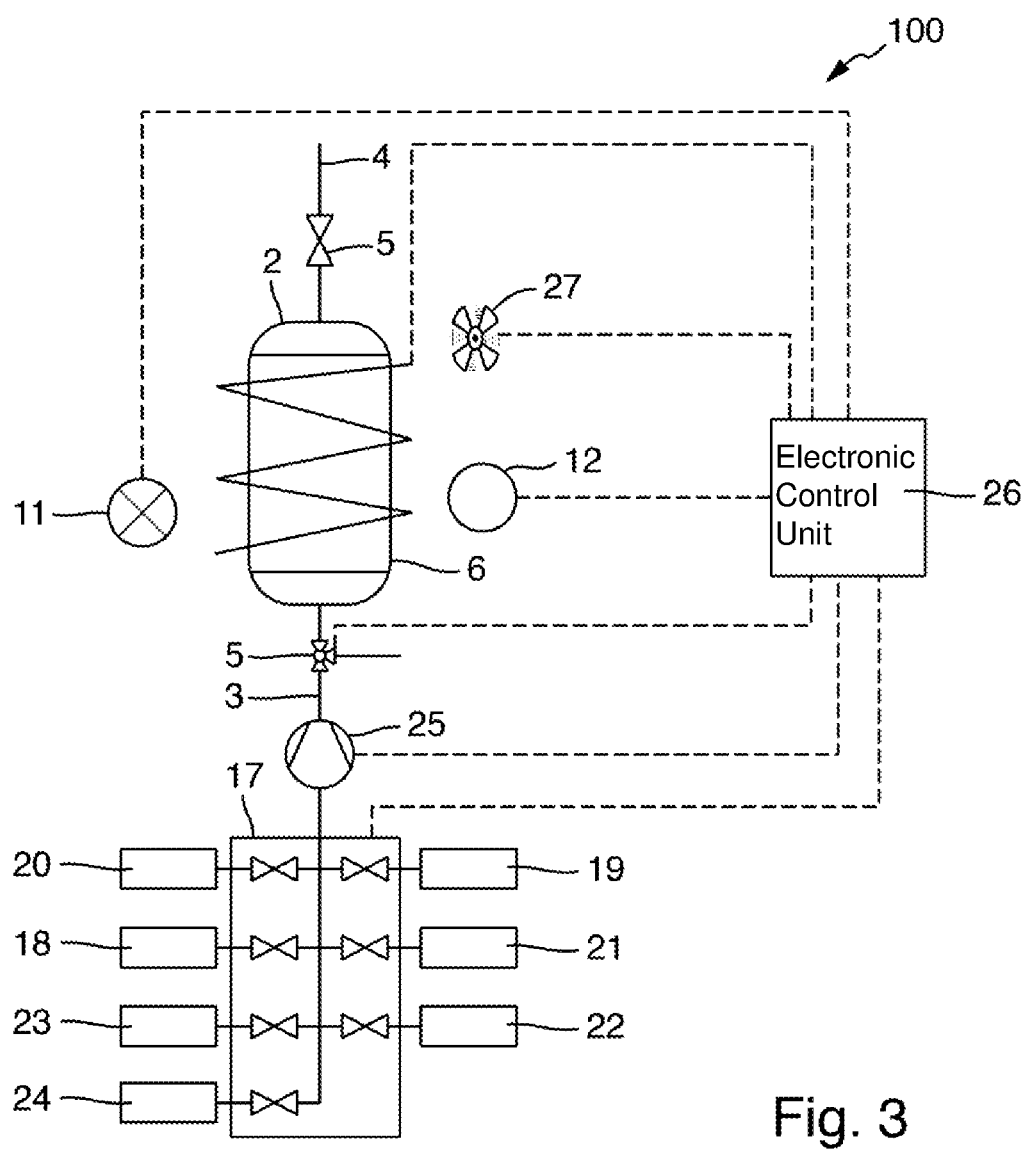
FIG. 3 shows a schematic basic illustration of an analysis device comprising a measuring arrangement according to the first exemplary embodiment.

FIG. 3 schematically shows a measuring arrangement 100 for measuring a total nitrogen content of a sample. The measuring arrangement 100 forms an analyzer operating in a completely automated manner.

Components that can be designed identically to the corresponding components of the measuring arrangement 1 shown in FIG. 1 or of the vessel 20 shown in FIG. 2 are denoted by identical reference numerals as in FIGS. 1 and 2.

The measuring arrangement 100 comprises a vessel 2 into which a fluid line 3 and a pressure equalization line 4 lead. The vessel 2 includes a housing wall 6 made of a metal alloy, in which two mutually opposing windows made of sapphire are inserted in a pressure-tight manner (not shown in FIG. 3). A heating wire extending spirally around the outer wall of the vessel 2 is used for controlling the temperature of a liquid accommodated in the interior of the vessel 2. A radiation source 11 and a radiation receiver 12 are arranged outside the vessel 2. The radiation source 11 is configured to emit measuring radiation of one or more predefined wavelengths in the UVC range of the electromagnetic spectrum. For example, the radiation source 11 may be a flash lamp. The radiation receiver 12 is configured to receive the measuring radiation and convert it into an electrical measurement signal. For example, it may comprise one or more photodiodes. The radiation source 11 and the radiation receiver 12 are arranged with respect to the windows in the housing wall 6 of the vessel 2 in such a way that measuring radiation enters the interior of the vessel 2 through one of the windows, passes through the interior of the vessel, and thus also through a liquid accommodated in the vessel, and exits through the other window and impinges on the radiation receiver 12.

The fluid line 3 leading into the vessel 2 is fluidically connected via a valve assembly 17 to a sample receiver 18 and a plurality of liquid containers 19, 20, 21, 22, 23, 24. The sample receiver 18 may be a vessel containing a larger quantity of a sample liquid taken from a body of water, a basin, or a process container, such as a reactor or a liquid line of a process plant. A liquid sample of a certain volume can be taken from the sample receiver 18 for analysis. It is also possible for the measuring arrangement 100 to be configured to take the liquid sample directly from a body of water, a basin or a process container.

The liquid container 19 contains a digestion reagent, which is to be added to the liquid sample in order to convert all nitrogen that is present in the sample and bound in chemical compounds into nitrate. The digestion reagent can, for example, be an alkaline solution of a strong oxidizing agent, for example peroxodisulfate.

The liquid container 20 contains another reagent to be added to the liquid sample after digestion, for example an acid used to neutralize the mixture of the sample liquid and the digestion reagent.

The liquid containers 21 and 22 contain a standard solution for calibration measurements. The standard solutions may be zero standards, i. e. solutions free of nitrogen-containing compounds, and/or solutions containing a particular predefined proportion of nitrogen bound in compounds.

The liquid container 23 contains a diluting solution, i.e. a solution which is free of nitrogen-containing compounds. This solution can optionally be added to the liquid sample.

The liquid container 24 serves as a collection container for consumed liquids.

In the present example, the measuring arrangement 100 comprises a peristaltic pump 25 for transporting liquid from the sample receiver 18 or the liquid containers 19 to 24 into the vessel 2. The peristaltic pump 25 is arranged in a fluid line connecting the fluid line 3 leading into the vessel 2 to the valve assembly 17. Via the valve assembly 17 and various fluid lines, each connected to one of the liquid containers 19 to 24 and the sample receiver 18, the peristaltic pump 15 and the vessel 2 can be connected to the liquid containers 19 to 24 and to the sample receiver 18 so as to meter liquids into the vessel 2 and/or to discharge liquid from the vessel 2 into the collection container 24. The peristaltic pump 25, the fluid lines, the valve assembly 17 and the valves 5 form a metering unit of the measuring arrangement 100 which is used to transport and meter the liquids to be used for the measurement and for calibration measurements.

In the present example, a combination of a single peristaltic pump with multiple valves and a valve assembly is used to transport and meter the fluids. A plurality of variants are possible, which achieve the same purpose. For example, multiple pumps can be provided, which are used to transport different liquids in each case. Accordingly, the number of valves is reduced. Instead of one or more peristaltic pumps, other pumps, for example, diaphragm pumps or piston pumps, can be used.

In order to operate the measuring arrangement 100 in a completely automated manner for determining measured values of the total nitrogen content, the measuring arrangement comprises an electronic control unit 26, which is designed as a computer, as a measurement transmitter, as a memory-programmable logic controller or as another data processing device that can be used for data processing and process control. The control unit 26 is connected to the heating wire, a fan 27 and a temperature sensor (not shown in FIG. 3) arranged in the vessel 2 in order to automatically regulate the temperature of a liquid present in the vessel 2 based on a predefined operating program. The control unit 26 is also connected to the radiation source 11 and the radiation receiver 12, in order to control the radiation source for the emission of measuring radiation, and to receive and further process signals of the radiation receiver 12 according to an evaluation program executable by the control unit 26, so as to ascertain measured values of the total nitrogen content of the liquid sample based on the signals of the radiation receiver 12.

The control unit 26 is moreover connected to the valves 5 and the valve device 7 as well as to the pump 25 so as to carry out a digestion of the liquid sample as well as, if necessary, a subsequent neutralization and/or dilution of the solution formed as a result of the digestion, intermittent calibration measurements and possibly rinsing steps in order to avoid entrainment between individual analysis cycles, according to a sequence predefined by the operating program.

A determination of the total nitrogen content of a liquid by means of the measuring arrangements illustrated in FIGS. 1 to 3 can take place in the following way: In a first step, a certain volume of a liquid is transported as a liquid sample from the sample receiver 18 into the vessel 2. In a second step, depending on the measuring range, the sample is diluted with a defined quantity of diluting liquid from the container 23, or left undiluted in vessel 2. In a third step, a predefined amount of the digestion reagent, an alkaline solution of peroxodisulfate in the present example, is transported from the liquid container 19 into the vessel 2, and the reaction mixture thus formed in the vessel 2 is heated by means of the heating element 13 with the vessel 2 closed in a pressure-tight manner (valves 5 closed). Under pressure, temperatures up to 120° C. can be achieved in the vessel 2. This temperature is maintained for a period of 20 minutes to one hour. Ideally, the total nitrogen bound in the liquid sample is converted into nitrate by the alkaline digestion. Thereafter, the reaction mixture is diluted in the vessel 2, and neutralized, by adding the acid from container 20.

The solution thus obtained is cooled to a target temperature, and a photometric measurement for ascertaining the nitrate content is carried out at the target temperature. The photometric measurement comprises irradiating measuring radiation of wavelengths 220 nm and 275 nm into the reaction mixture, and detecting the measuring radiation after passing through the reaction mixture by means of the radiation receiver 12. Radiation of the wavelength 220 nm is absorbed by nitrate, so that the transmission or absorption of radiation of this wavelength is a measure of the nitrate content of the liquid sample. The second wavelength 275 nm is used to correct influences of interfering substances and the turbidity of the liquid sample.

The nitrate content correlates with the total nitrogen content of the liquid sample, so that a value of the parameter TN can be ascertained from the measurement signals of the photometric measurement based on an assignment rule (e.g. table or calibration function) ascertainable by calibration. Based on this relationship, the electronic control unit 25 ascertains a value for the total nitrogen content of the liquid sample from the measurement signals of the radiation receiver 12.

All these steps are carried out completely automatically by means of the electronic control unit 26.

Figure 4:
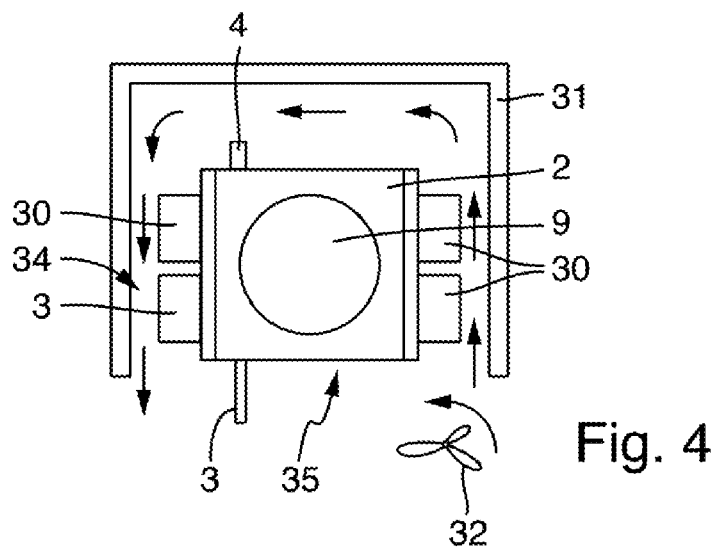
FIG. 4 shows a schematic longitudinal sectional view of a vessel of a measuring arrangement according to a third exemplary embodiment.
Figure 5:
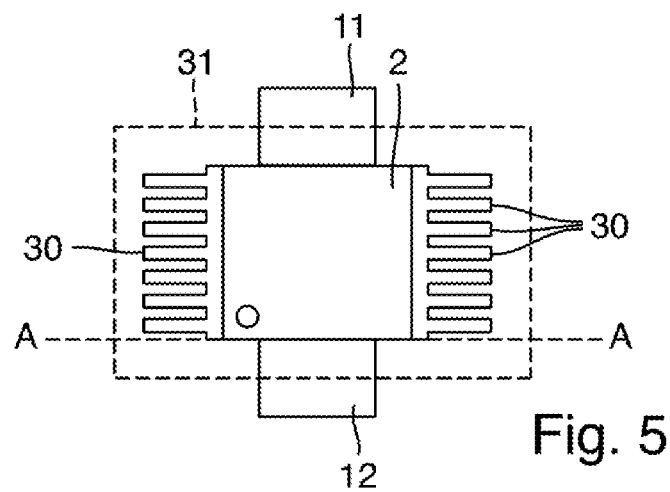
FIG. 5 shows a schematic illustration of the vessel shown in FIG. 4, viewed from above.
Figure 6:
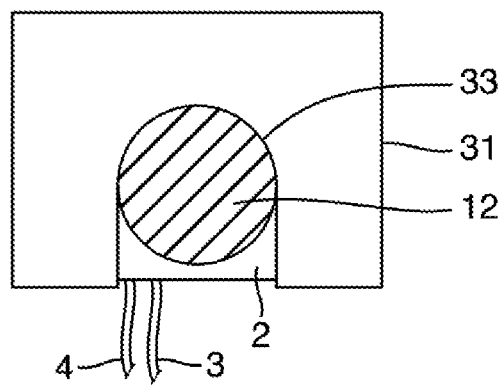
FIG. 6 shows a schematic illustration of the vessel shown in FIGS. 4 and 5 in a side view.

FIGS. 4, 5 and 6 schematically show an arrangement comprising a vessel 2 and an attachment 31 for use in a measuring arrangement according to a third exemplary embodiment, which can otherwise be designed identically to the measuring arrangement 100 described based on FIG. 3. FIG. 5 shows the vessel 2 in a view from above, and FIG. 4 shows it in a sectional view along the sectional plane A-A shown in FIG. 5. FIG. 6 shows the vessel 2 in a side view in a direction perpendicular to the viewing direction shown in FIG. 5.

In the exemplary embodiment shown in FIGS. 4, 5 and 6, the vessel 2 has an essentially cuboid or cubic shape. The vessel may be formed from a metal or a metal alloy, in the present example the vessel 2 is made of titanium. The vessel wall can also consist of multiple components, wherein a surface intended for contact with a reaction mixture accommodated in the vessel 2 is formed from a chemically stable material, for example titanium, gold, a ceramic or a high-performance plastic. Fluid lines 3 and 4 lead into the vessel 2, which, as in the exemplary embodiments described above, are used to introduce fluids into the vessel 2 and to discharge fluids from the vessel 2. Openings 9 are provided on two mutually opposing sides of the vessel, in which mutually opposing windows made of sapphire are inserted in a pressure-tight manner.

The vessel 2 furthermore comprises a heating element, for example a heating resistor or a heating wire, which is not shown in FIGS. 4 to 6 for the sake of improved clarity. Cooling elements 30 are arranged on two further mutually opposing sides of the vessel 2. In the present example, the cooling elements 30 are designed in the form of individual cooling ribs and are formed from a different material than the vessel 2, namely aluminum or another metal having the best possible thermal conductivity and the lowest possible thermal capacity. They may be formed from a combination of multiple materials. The heat sinks 30 are connected to the vessel wall of the vessel 2 via connecting means, for example screws. To improve the heat-conducting contact between the vessel wall and the cooling elements 30, a heat-conductive paste applied at the joint may be used.

In the exemplary embodiment shown in FIGS. 4, 5 and 6, the vessel 2 is surrounded by an attachment 31, which is open on one side. In FIG. 5, the attachment 31 is only hinted at by dashed lines. The attachment 31 has an open side, which serves as an opening 35 leading into the space 34 surrounding the cooling elements 30 for supplying air from the surrounding area to the cooling elements 30. To this end, a fan 32 is arranged at the opening 35 of the attachment 31 and is configured to generate an air flow flowing around the cooling elements 30 so as to dissipate heat from the cooling elements 30. The air flow through the attachment 31 when the fan 32 is running is illustrated in FIG. 4 by arrows.

On two mutually opposing sides, the attachment 31 has a recess 33 (FIG. 6) into which housings of the light source 11 and of the photoreceiver 12 of the measuring arrangement fit. The attachment 31 can thus be placed over the vessel 2 in the manner of a hood. Tubes 3 and 4, via which fluids can be transported into the vessel 2 and out of the vessel 2, can be led out of the open side of the attachment 31, as shown in FIG. 6.

The heat dissipation from the vessel 2 during cooling of the reaction mixture can be carried out more efficiently by means of the heat sinks 30, which accelerates the cooling of a reaction mixture present in the vessel 2 to a target temperature. When the target temperature is reached more quickly, the above-described photometric measurement can be performed earlier, and thus the time required for a measuring cycle can be shortened. On the other hand, although the cooling elements 30 increase the thermal mass of the overall device to be heated, an acceptable heating time for the reaction mixture can be achieved, despite the additional thermal mass, by suitable control of the heating power, even if no additional measures are taken.

The attachment 31 surrounding the vessel 2 in the exemplary embodiment shown here is used to minimize the required heating power by retaining warm air in the upper, closed region of the attachment 31 during heating phases when the fan 32 is switched off. Heat loss via the heat sinks 30 during the heating phase is thus counteracted. So as to amplify this effect, the attachment 31 is advantageously made of a thermally insulating material, for example of a plastic. Additionally or alternatively, the attachment 31 may comprise an insulating material, for example a thermally insulating foam plastic.

Using the very simple measures described here, the measuring cycle time, in particular that for heating and cooling the reaction mixture made of the sample and the reagents, can be effectively shortened, without the need for complex active cooling measures, e.g. the use of fluid cooling, heat exchangers or Peltier elements. This can be applied particularly advantageously in the above-described measuring arrangement 100 for measuring the total nitrogen bound in a measuring liquid, which is configured to carry out the digestion of the liquid sample, by adding an oxidizing agent and heating the reaction mixture thus formed, and the subsequent photometric measurement at a defined target temperature in the range of room temperature in one and the same vessel.

If the arrangement shown in FIGS. 4 to 6 is used in a measuring arrangement such as the measuring arrangement 100 illustrated in FIG. 3 for carrying out the above-described method for determining the total nitrogen content of a liquid, the heating of the reaction mixture by way of the heating element comprises controlling the heating power of the heating element when the fan 32 is switched off, so as to set a rapid heating rate and thereafter a constant temperature of the reaction mixture for digestion of the nitrogen-containing compounds. The cooling comprises switching on the fan 32 when the heating element is switched off so as to reach the target temperature for the photometric measurement with a rapid cooling rate. This can be carried out in an automated manner by the control unit 26 of the measuring arrangement 100.

Figure 7:
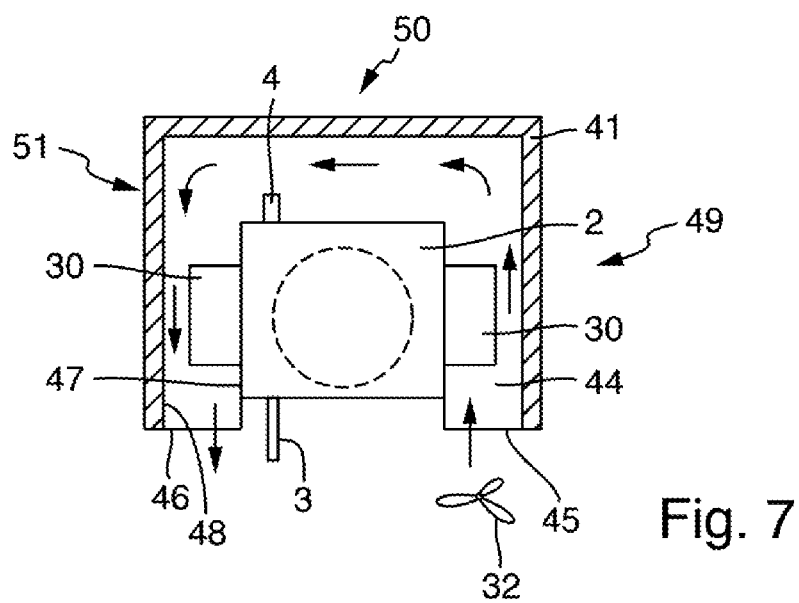
FIG. 7 shows a schematic longitudinal sectional view of a vessel of a measuring arrangement according to a fourth exemplary embodiment.
Figure 8:
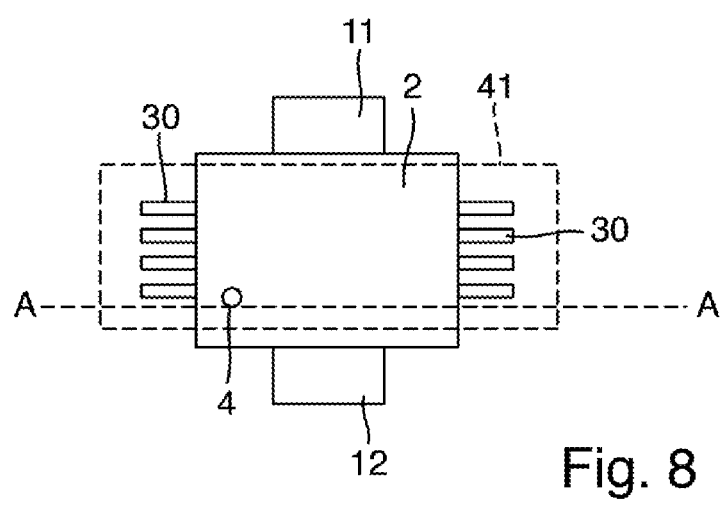
FIG. 8 shows a schematic illustration of the vessel shown in FIG. 6, viewed from above.

FIGS. 7 and 8 schematically show an arrangement comprising a vessel 2 and an attachment 41 for use in a measuring arrangement according to a fourth exemplary embodiment, which can otherwise be designed identically to the measuring arrangement 100 described based on FIG. 3. FIG. 8 shows the vessel 2 in a view from above, and FIG. 7 shows it in a sectional view along the sectional plane A-A illustrated in FIG. 8.

The vessel 2 comprising cooling elements 30 has essentially the same design as the vessel 2 of the third exemplary embodiment illustrated in FIGS. 4 to 6. Identically configured parts are denoted by identical reference numerals. The attachment 41, which accommodates the regions of the vessel 2 provided with cooling elements 30, is placed over the vessel 2 in the exemplary embodiment shown here. A space 44 surrounding the cooling elements 30 is formed between the wall 48 of the attachment 41 and the vessel wall 47 of the vessel 2. This space 44 has the shape of a U-shaped channel having an inlet opening 45 and an outlet opening 46. A fan 32 is arranged at the inlet opening 45, which is configured to generate a gas flow through the channel from the inlet opening 45 to the outlet opening 46 (direction of arrow in FIG. 7). In the flow direction, proceeding from the inlet opening 45, the channel includes a first section 49 extending upwardly parallel to a first side wall of the vessel 2. Furthermore, downstream of the first section, the channel includes a second section 50 extending around the vessel 2 at the upper end of the vessel 2. Downstream, a third section 51 adjoins the second section 50 and extends downwardly to the outlet opening 46, parallel to a side wall located opposite the first side wall of the housing 2. Air or gas transported through the U-shaped channel thus flows along the cooling elements 30 around the vessel 2. The arrangement according to this fourth exemplary embodiment otherwise has the same functions and advantages as the arrangement according to the third exemplary embodiment described based on FIGS. 4 to 6. It can also be used in a measuring arrangement such as the measuring arrangement 100 described in connection with FIG. 3 in order to optimize heating and cooling times.

The invention claimed is:

1. A measuring arrangement for measuring a total nitrogen bound in a measuring liquid, comprising:
   a radiation source designed to emit at least measuring radiation of a wavelength or wavelength range in an ultraviolet wavelength range;
   a radiation receiver configured to generate a signal that depends on an intensity of measuring radiation impinging on the radiation receiver;
   a vessel having a vessel wall that encloses an interior space and is embodied of a first material, the vessel wall having a first opening closed by a first window and further having a second opening opposite the first opening and closed by a second window, wherein the first and second windows are embodied of a second material and are transparent to the measuring radiation;
   a heating element in thermal contact with the vessel wall;
   a plurality of cooling elements attached on an outer side of the vessel and in thermal contact with the vessel wall;
   a thermally insulating hood embodied to surround the vessel and the attached cooling elements such that a channel for air passage is formed between the vessel and the hood, wherein the channel begins at an inlet opening between the hood and the vessel at a first side of the vessel, follows a U-shaped path up along the first side of the vessel, along a top side of the vessel, and down along a second side of the vessel, and ends at an outlet opening between the hood and the vessel at the second side of the vessel; and
   a ventilation system including at least one fan arranged at the inlet opening of the channel and configured to transport air into the channel such that the air flows through the U-shaped path of the channel and across the cooling elements, wherein the air exits the channel at the outlet opening of the channel,
   wherein the radiation source and the radiation receiver are arranged with respect to the vessel such that at least a portion of the measuring radiation emitted by the radiation source propagates along a measuring path extending from the radiation source through the first window, the vessel, and the second window to the radiation receiver.

2. The measuring arrangement according to claim 1, wherein the outlet opening and the inlet opening are arranged at a same height.

3. The measuring arrangement according to claim 1, wherein the vessel includes at least one liquid inlet embodied to fluidically connect to a sample receiver containing the measuring liquid.

4. The measuring arrangement according to claim 3, wherein the vessel further includes a pressure equalization opening.

5. The measuring arrangement according to claim 3, further comprising:
   a liquid container containing a digestion reagent having a pH of at least 12, wherein the liquid container is fluidically connectable to the at least one liquid inlet.

6. The measuring arrangement according to claim 1, wherein the first material is a metal, a metal alloy, a ceramic, or a high-performance plastic.

7. The measuring arrangement according to claim 1, wherein the second material is sapphire, diamond, magnesium fluoride, calcium fluoride, or barium fluoride.

8. The measuring arrangement according to claim 1, wherein the first and the second windows each have two plane-parallel surfaces extending essentially perpendicularly to the radiation path.

9. The measuring arrangement according to claim 1, wherein the first and/or the second window each have at least one curved surface that enables beam shaping of the measuring radiation.

10. The measuring arrangement according to claim 5, further comprising:
   a first liquid path extending from the sample receiver to the at least one liquid inlet;
   a second liquid path extending from the liquid container to the at least one liquid inlet;
   at least one metering unit, which comprises at least one pump and/or at least one valve arranged in the first and/or second liquid paths and is configured to transport a predefined amount of liquid along the first liquid path into the vessel, and is furthermore configured to transport a predefined amount of liquid from the liquid container along the second liquid path into the vessel; and
   an electronic control unit, which is configured to control the metering unit to transport measuring liquid and digestion reagent into the vessel, to control the heating element for controlling a temperature of liquid present in the vessel, to excite the radiation source to emit the measuring radiation, and to detect and process signals of the radiation receiver.

11. The measuring arrangement according to claim 1, wherein the hood includes, on each of two mutually opposing sides, a recess into which housings of the radiation source and of the radiation receiver are fit.

* * * * *